US012376966B2

(12) United States Patent
Klingseis et al.

(10) Patent No.: US 12,376,966 B2
(45) Date of Patent: Aug. 5, 2025

(54) INTERVERTEBRAL IMPLANT

(71) Applicant: Aesculap AG, Tuttlingen (DE)

(72) Inventors: Susanne Klingseis, Biberach (DE); Irene Marx, Trossingen (DE); Patricia Graf, Tuttlingen (DE); Julian Reck, Scheer (DE); Marie Salome Knubben-Belik, Rottweil (DE); Mandy Kleinwechter, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 205 days.

(21) Appl. No.: 17/882,546

(22) Filed: Aug. 6, 2022

(65) Prior Publication Data

US 2022/0370209 A1 Nov. 24, 2022

Related U.S. Application Data

(63) Continuation of application No. PCT/EP2021/052775, filed on Feb. 5, 2021.

(30) Foreign Application Priority Data

Feb. 6, 2020 (DE) ..................... 10 2020 103 015.0

(51) Int. Cl.
*A61F 2/44* (2006.01)
*A61F 2/30* (2006.01)

(52) U.S. Cl.
CPC ... *A61F 2/4455* (2013.01); *A61F 2002/30113* (2013.01); *A61F 2002/30878* (2013.01);
(Continued)

(58) Field of Classification Search
CPC ...... A61F 2/4455; A61F 2/4465; A61F 2/447; A61F 2002/30841; A61F 2002/30843;
(Continued)

(56) References Cited

U.S. PATENT DOCUMENTS 10,182,923 B2   1/2019   Willis et al.
10,299,938 B1   5/2019   Ehteshami
(Continued)

FOREIGN PATENT DOCUMENTS

CA   2530730 A1   12/2004
DE   9413778 U1    1/1996
(Continued)

OTHER PUBLICATIONS

Search Report received in International Application No. PCT/EP2021/052775 dated May 18, 2021, with translation, 5 pages.
(Continued)

*Primary Examiner* — Eduardo C Robert
*Assistant Examiner* — Anna V. Little
(74) *Attorney, Agent, or Firm* — Christopher A. Rothe; CM Law

(57) ABSTRACT

An intervertebral implant for insertion into an intervertebral disc space between two adjacent vertebral bodies of a human or animal spine. The intervertebral implant has an implant top side, which defines a first vertebral body abutment face for abutting against a first vertebral body, and an implant bottom side, which defines a second vertebral body abutment face for abutting against a second vertebral body. The intervertebral implant comprises a frame structure with at least two support elements. The at least two support elements extend from the implant top side to the implant bottom side. The at least two support elements define support element longitudinal axes, which run transversely, in particular perpendicularly, to the first and/or second vertebral body abutment face.

20 Claims, 8 Drawing Sheets

(52) U.S. Cl.
CPC .............. *A61F 2002/3092* (2013.01); *A61F 2002/4445* (2013.01)

(58) Field of Classification Search
CPC .. A61F 2002/30845; A61F 2002/30878; A61F 2002/3092
See application file for complete search history.

(56) References Cited

U.S. PATENT DOCUMENTS

| | | | |
|---|---|---|---|
| 2013/0030529 A1* | 1/2013 | Hunt .................. | A61F 2/30771 623/16.11 |
| 2017/0156880 A1* | 6/2017 | Halverson ............ | A61F 2/4455 |
| 2019/0083282 A1* | 3/2019 | Roeder .................. | A61L 27/56 |
| 2019/0151113 A1* | 5/2019 | Sack .................... | A61F 2/4455 |
| 2019/0151114 A1 | 5/2019 | Sack | |
| 2019/0183653 A1* | 6/2019 | Gregersen .............. | A61F 2/447 |
| 2019/0254840 A1 | 8/2019 | Gray et al. | |
| 2019/0274841 A1* | 9/2019 | Hawkes ................ | A61F 2/442 |
| 2019/0343651 A1* | 11/2019 | Ryan .................... | A61F 2/4455 |

FOREIGN PATENT DOCUMENTS

| | | |
|---|---|---|
| JP | 2007504843 A | 3/2007 |
| WO | 2018169873 A1 | 9/2018 |

OTHER PUBLICATIONS

Written Opinion received in International Application No. PCT/EP2021/052775 dated May 18, 2021, with translation, 12 pages.

\* cited by examiner

INTERVERTEBRAL IMPLANT

CROSS-REFERENCE TO RELATED APPLICATIONS

This application is a continuation of International Application No. PCT/EP2021/052775, filed on Feb. 5, 2021, and claims priority to German Application No. 10 2020 103 015.0, filed on Feb. 6, 2020.

The present disclosure relates to the subject matter disclosed in International Application No. PCT/EP2021/052775, filed on Feb. 5, 2021, and in German Application No. 10 2020 103 015.0, filed on Feb. 6, 2020, the contents of both applications being incorporated herein by reference in their entireties and for all purposes.

FIELD

The present disclosure relates to intervertebral implants for insertion into an intervertebral disc space between two adjacent vertebral bodies of a human or animal spine generally, and more specifically to an intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body.

BACKGROUND

Intervertebral implants of the kind described at the outset are known in various embodiments. They are inserted into an intervertebral disc space as a replacement for the associated damaged intervertebral disc between two vertebral bodies in order to connect the adjacent vertebral bodies to one another and thus stiffen the spine on a portion comprising two vertebral bodies.

Large forces exerted by the adjacent vertebral bodies on the implant top side and the implant bottom side act on the intervertebral implant. Therefore, it is important that for maintaining the height of the intervertebral disk space, i.e., the distance between the adjacent vertebral bodies, the intervertebral implant has sufficient stability in order to avoid injury to the nerves running in the spinal canal. In particular in the case of open-pored structures that are used as intervertebral implants, there is relatively easily a risk of the intervertebral implant being deformed overall due to compression and thus a height of the intervertebral disc space not being able to be maintained. An undesired consequence of this may be, in particular, damage to vessels and nerves emerging between the vertebral bodies as well as to nerves running in the spinal canal.

SUMMARY

In a first aspect of the present disclosure, an intervertebral implant for insertion into an intervertebral disc space between two adjacent vertebral bodies of a human or animal spine is provided. The intervertebral implant has an implant top side, which defines a first vertebral body abutment face for abutting against a first vertebral body, and an implant bottom side, which defines a second vertebral body abutment face for abutting against a second vertebral body. The intervertebral implant comprises a frame structure with at least two support elements. The at least two support elements extend from the implant top side to the implant bottom side. The at least two support elements define support element longitudinal axes, which run transversely, in particular perpendicularly, to the first and/or second vertebral body abutment face.

In a second aspect of the present disclosure, an intervertebral implant for insertion into an intervertebral disc space between two adjacent vertebral bodies of a human or animal spine is provided. The intervertebral implant has an implant top side, which defines a first vertebral body abutment face for abutting against a first vertebral body, and an implant bottom side, which defines a second vertebral body abutment face for abutting against a second vertebral body. The intervertebral implant comprises a frame structure with at least two support elements. The at least two support elements extend from the implant top side to the implant bottom side. The at least two support elements define support element longitudinal axes, which run transversely, in particular perpendicularly, to at least one of the first vertebral body abutment face and the second vertebral body abutment face. The frame structure comprises a first self-enclosed inner frame part and a second self-enclosed inner frame part. The at least two support elements connect the two inner frame parts to one another by a direct connection of the inner frame parts to the at least two support elements.

In a third aspect of the present disclosure, an intervertebral implant for insertion into an intervertebral disc space between two adjacent vertebral bodies of a human or animal spine is provided. The intervertebral implant has an implant top side, which defines a first vertebral body abutment face for abutting against a first vertebral body, and an implant bottom side, which defines a second vertebral body abutment face for abutting against a second vertebral body. The intervertebral implant comprises a frame structure with at least two support elements. The at least two support elements extend from the implant top side to the implant bottom side. The at least two support elements define support element longitudinal axes, which run transversely, in particular perpendicularly, to at least one of the first vertebral body abutment face and the second vertebral body abutment face. The frame structure comprises a first self-enclosed inner frame part and a second self-enclosed inner frame part. The at least two support elements connect the two inner frame parts to one another. The at least two support elements define a cross sectional area that is constant or substantially constant along its extent.

BRIEF DESCRIPTION OF THE DRAWING FIGURES

The foregoing summary and the following description may be better understood in conjunction with the drawing figures, of which:

DETAILED DESCRIPTION

Figure 1:
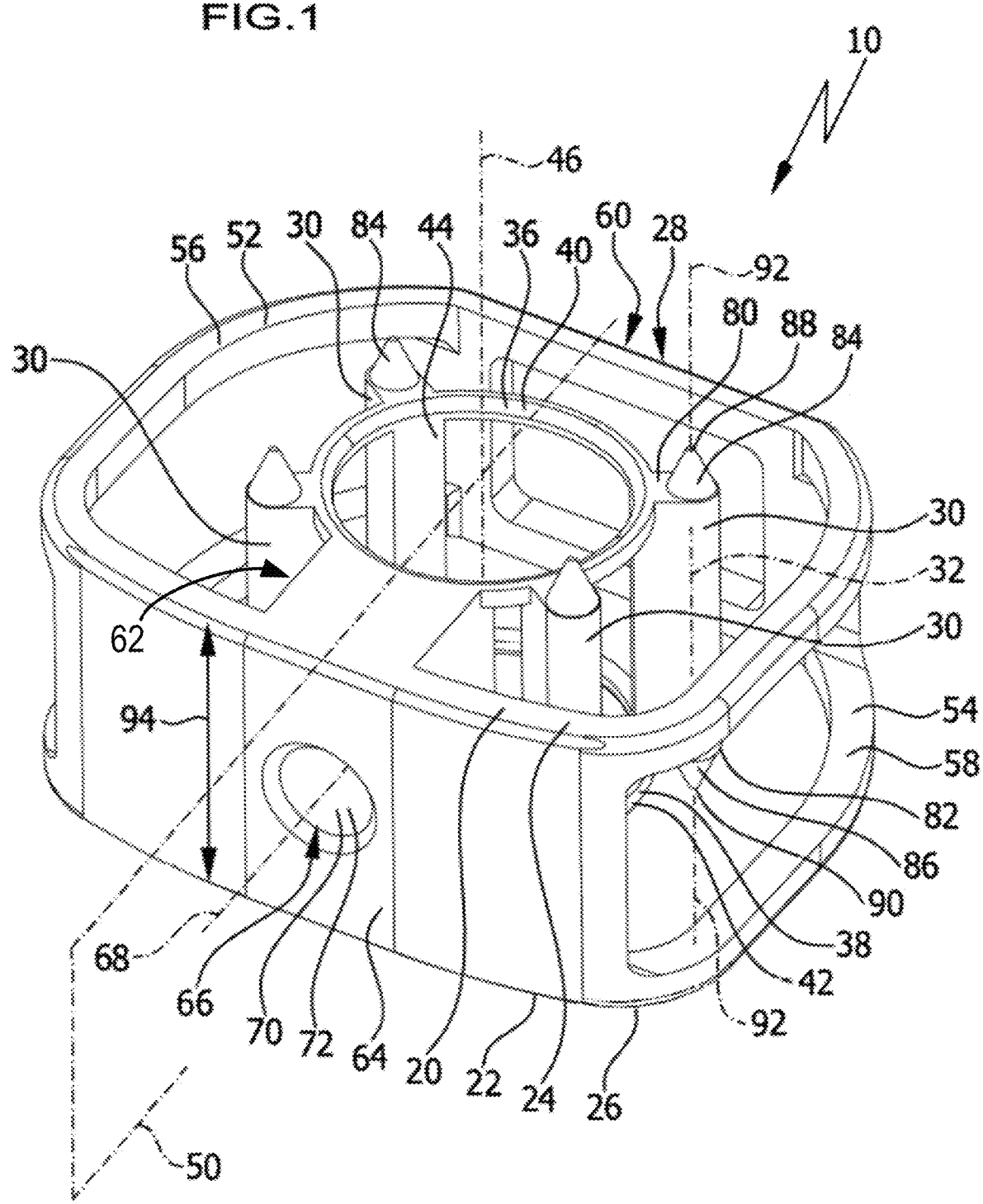
FIG. 1 is a schematic perspective total view of a first embodiment of an intervertebral implant.
Figure 2:
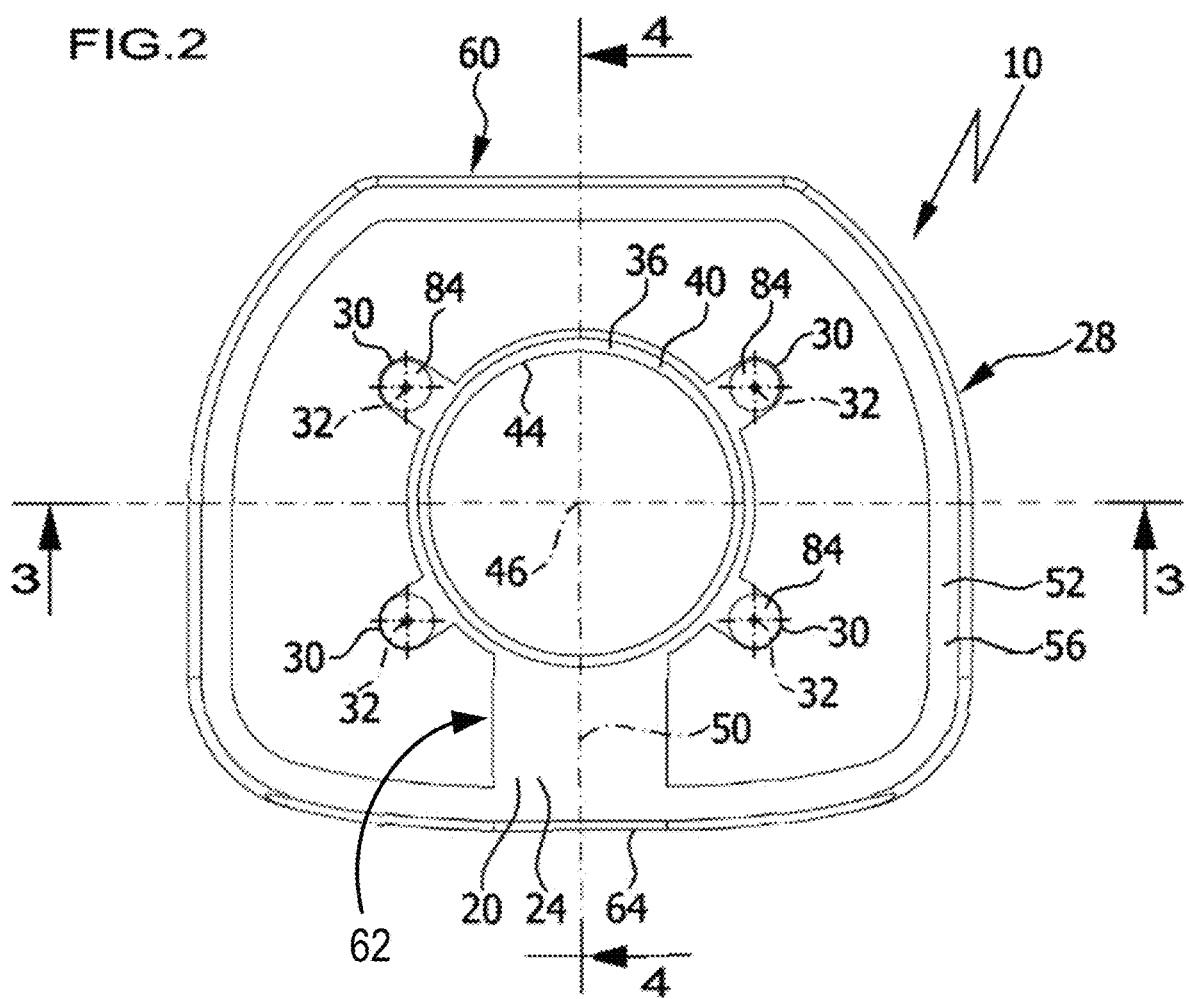
FIG. 2 is a plan view of the intervertebral implant of FIG. 1.
Figure 3:
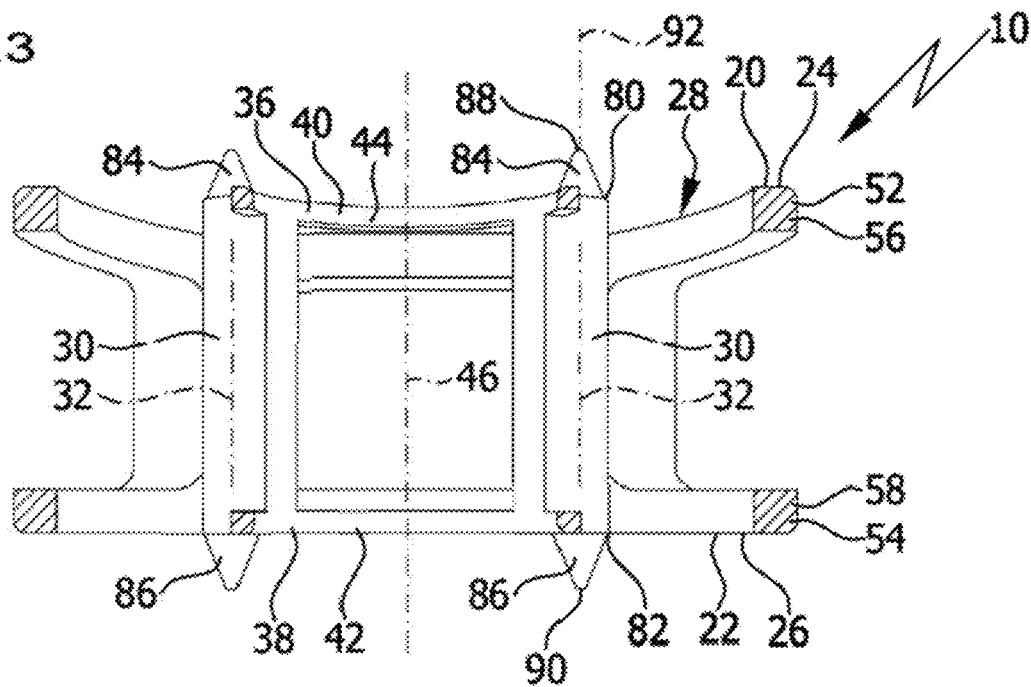
FIG. 3 is a cut view along line 3-3 in FIG. 2.
Figure 4:
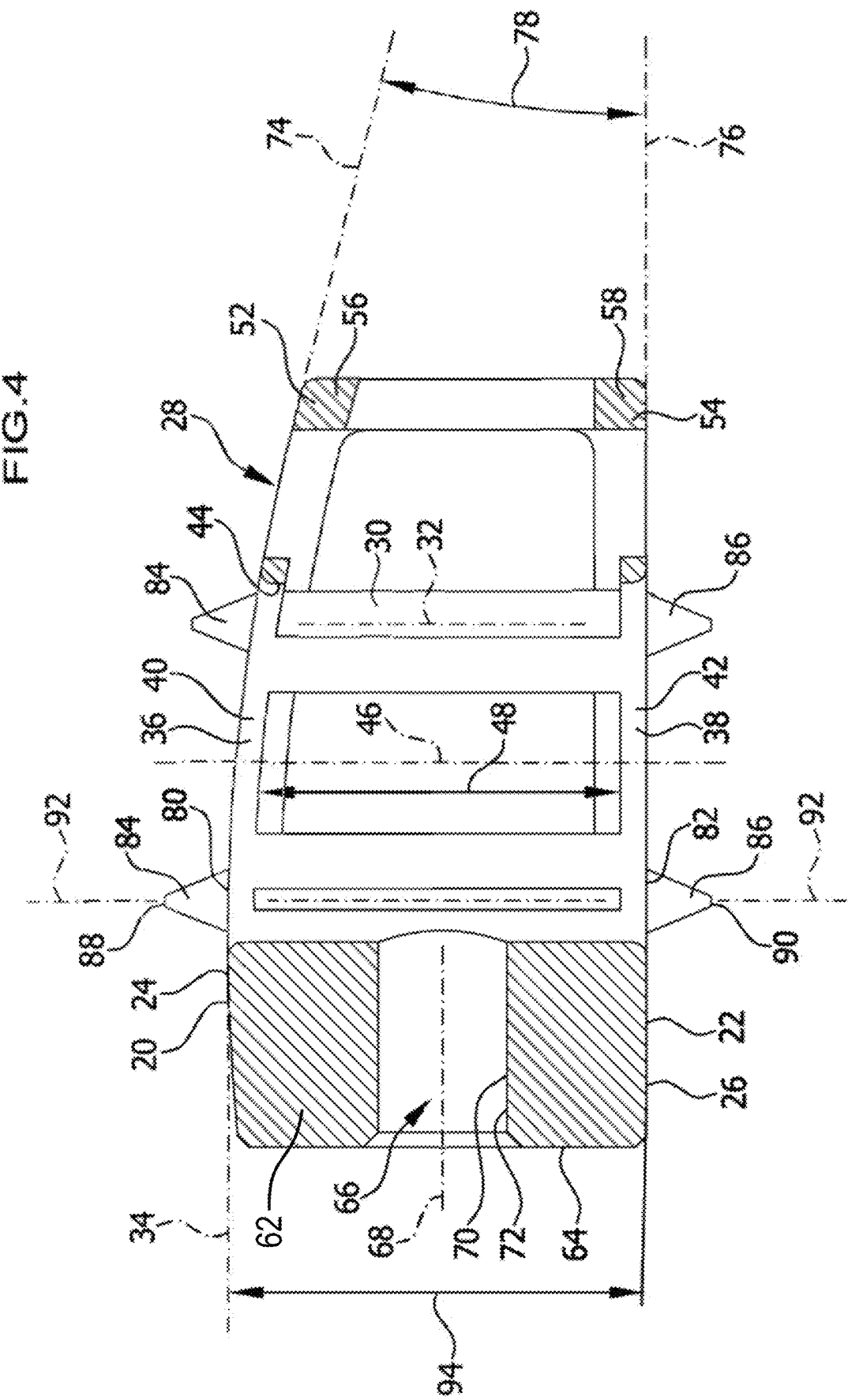
FIG. 4 is a cut view along line 4-4 in FIG. 2.
Figure 5:
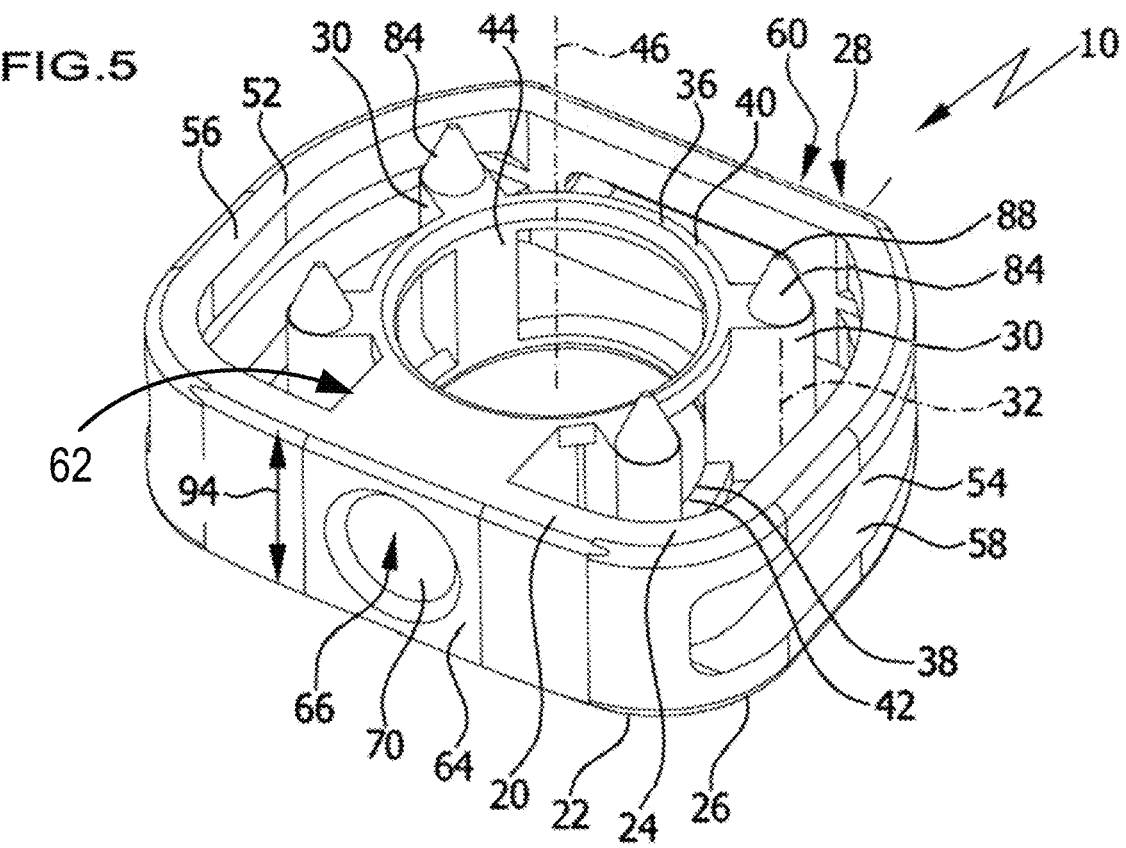
FIG. 5 is a schematic perspective total view of a further embodiment of an intervertebral implant.
Figure 6:
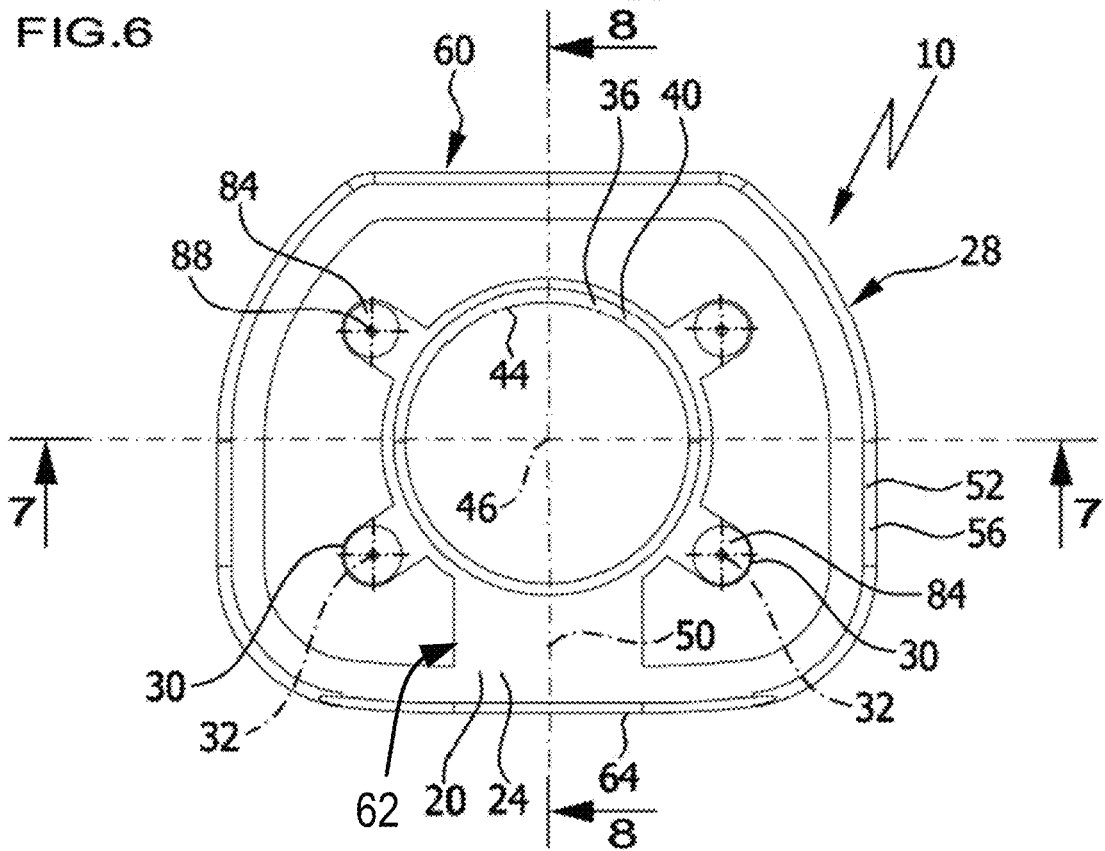
FIG. 6 is a plan view of the intervertebral implant from FIG. 5.
Figure 7:
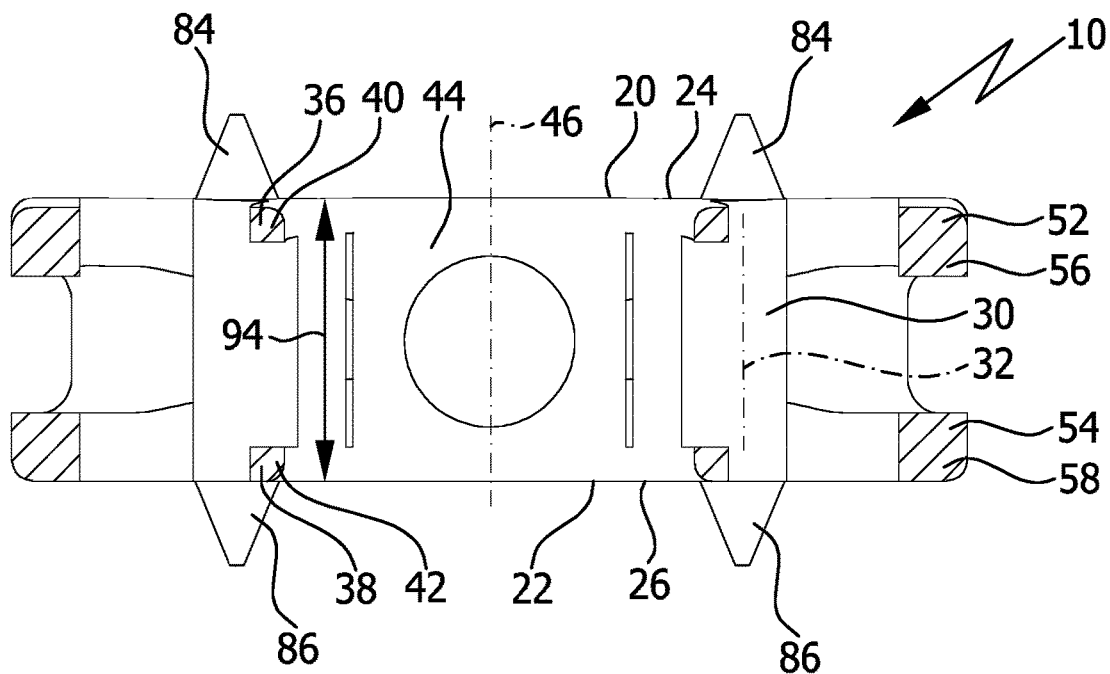
FIG. 7 is a cut view along line 7-7 in FIG. 6.
Figure 8:
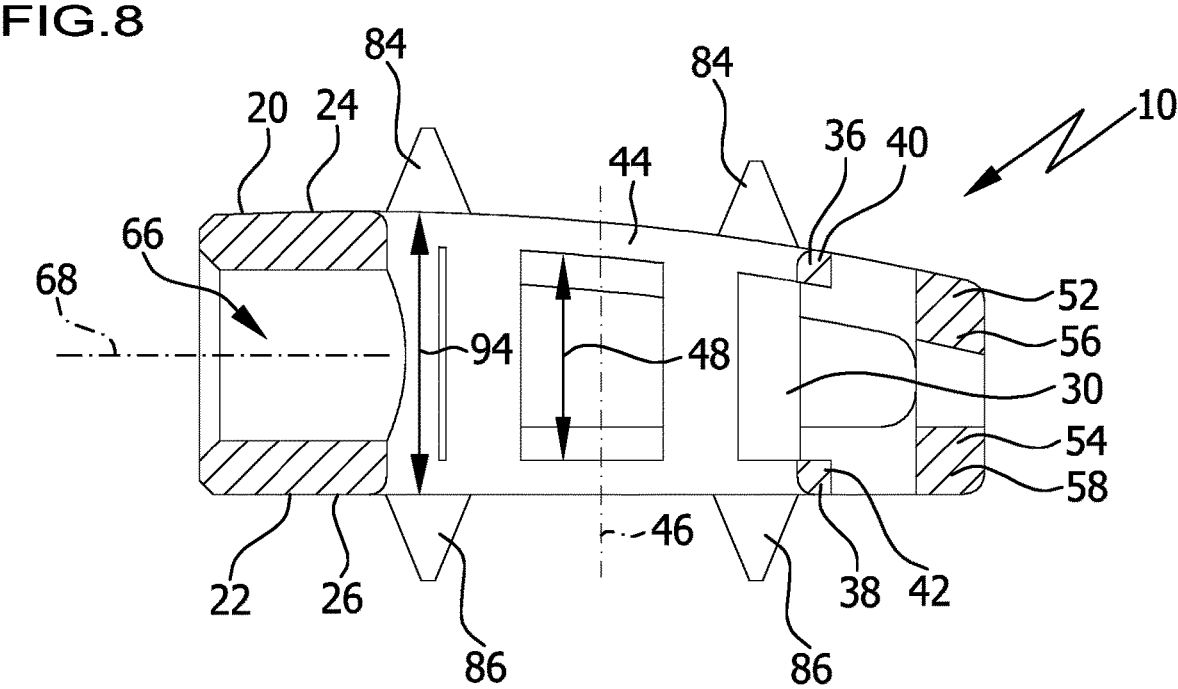
FIG. 8 is a cut view along line 8-8 in FIG. 6.

Although the present disclosure is illustrated and described herein with reference to specific embodiments, the present disclosure is not intended to be limited to the details shown. Rather, various modifications may be made in the details without departing from the intended scope.

The present disclosure relates to an intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body, wherein the intervertebral implant comprises a frame structure with at least two support elements, wherein the at least two support elements extend from the implant top side to the implant bottom side, and wherein the at least two support elements define support element longitudinal axes, which run transversely, in particular perpendicularly, to the first and/or second vertebral body abutment face.

Providing such a frame structure with the at least two support elements has the advantage, in particular, that forces acting on the implant top side and the implant bottom side can be transmitted directly into the at least two support elements. A compression of the intervertebral implant and thus a reduction of the height of the intervertebral disc space into which the intervertebral implant is inserted can thus be avoided in a significantly better manner. In addition, the at least two support elements also make it possible, in particular, to arrange anchoring projections, so-called spikes, on their ends, which can reach, for example, up to the implant top side and up to the implant bottom side. These can thus be optimally joined, in particular, to intervertebral implants that consist predominantly of an open-pored lattice structure, which may be formed, e.g., by additive or generative production methods. An open-pored structure is desirable, in particular, for enabling the ingrowth of bone into the intervertebral implant. Moreover, the support elements facilitate the cleaning of the intervertebral implant, in particular after the production thereof, namely, for example, when the intervertebral implant comprises an open-pored lattice structure. Unwashable areas that typically arise when the anchoring projections are attached directly to the open-pored lattice structure are reduced to a minimal level due to the arrangement on the support elements for washing out the intervertebral implant after production, for example to remove possible auxiliary agent residues. The frame structure may, in particular, be of multi-part configuration, wherein the at least two support elements can join the plurality of components of the frame structure to one another in order to thus obtain a solid and stable structure of the intervertebral implant overall. The at least two support elements may, in particular, be of rod-shaped configuration. Furthermore, the at least two support elements may define a cross sectional area that is constant or substantially constant along its extent. This serves, in particular, to reduce unwashable areas during the cleaning of the intervertebral implant. Due to the continuity of the at least two support elements, a cleaning of the intervertebral implant, in particular an open-pored lattice structure optionally comprised thereby, is made easier. For washing out the intervertebral implant after production, for example to remove possible auxiliary agent residues, unwashable areas can be reduced to as great an extent as possible.

It is advantageous if the at least two support elements have end faces that face away from the intervertebral implant and if at least one of these end faces bears at least one anchoring projection that points away from the intervertebral implant. Such an anchoring projection, also referred to as a spike, serves to securely position the intervertebral implant in the intervertebral disc space. The anchoring projections can dig into the adjacent vertebral bodies and thus prevent or at least delimit a relative movement between the intervertebral implant and the adjacent vertebral bodies. By arranging the anchoring projections on the end faces of the support elements, a reliable and solid connection thereof to the intervertebral implant is possible. The anchoring projections can thereby be securely prevented from being sheared off of the intervertebral implant. This risk exists, in particular, when such anchoring projections are arranged directly on open-pored lattice structures. This can lead to a deformation of the lattice structure and thus to the anchoring projections becoming dysfunctional, whether it be that the anchoring projections are pushed into the intervertebral implant or are bent over, such that they no longer point in the direction toward the adjacent vertebral bodies and can no longer penetrate into same to anchor the intervertebral implant.

To enable a sure anchoring of the intervertebral implant on the adjacent vertebral bodies, it is favorable if the at least one anchoring projection is of pointed, in particular thorn-like, configuration.

The intervertebral implant can be formed in a simple manner if the at least one anchoring projection is of conical or substantially conical configuration. It then has a tip that is helpful for digging into the adjacent vertebral bodies and can also be attached with its base face to the associated support element with a large area of contact.

It is favorable if the at least one anchoring projection defines a projection longitudinal axis and if the projection longitudinal axis extends in parallel or substantially in parallel to the support element longitudinal axis of the associated support element. As a result of the parallel or collinear alignment of the projection longitudinal axis and the support element longitudinal axis of the respective support element, a stability of the intervertebral implant and, in particular, an attachment of the at least one anchoring projection to the associated support element can be improved.

It is advantageous if the at least two support elements define a cross section in relation to the respective support element longitudinal axis, which is rectangular, triangular, or circular, or is formed by a combination of a rectangle and a semicircle. Support elements with cross sectional shapes of that kind can be formed in a simple manner. They have a sufficient stability for their intended purpose. In particular, they can be connected to a frame structure in a simple and secure manner due to their design.

In order to improve the stability of the intervertebral implant, it is favorable if the intervertebral implant comprises three or four support elements. They may be arranged, in particular, symmetrically in relation to a symmetry plane of the intervertebral implant that, for example, is of mirror-symmetrical configuration.

For increasing the stability of the intervertebral implant, it is favorable if the at least two support elements are of solid configuration. Solid means, in particular, that they are formed without cavities and thus form solid supports that help to avoid a compression between the implant top side and the implant bottom side.

In accordance with a further preferred embodiment of the present disclosure, provision may be made that the intervertebral implant has a central perforation and that the perforation extends from the implant top side to the implant bottom side through the intervertebral implant. The perforation can be used, in particular, to accommodate material conducive to bone growth, thereby improving the ingrowth of bone into the intervertebral implant and thus a stability of the connection between the adjacent vertebral bodies that the intervertebral implant connects to one another.

The intervertebral implant can be formed in a simple manner if the perforation is of hollow-cylindrical or substantially hollow-cylindrical configuration, or has an oval or rectangular, in particular square, cross section. Depending on the size and outer contour of the intervertebral implant, the shape of the perforation and, in particular, the cross sectional shape thereof can be selected to enable an optimal ingrowth of bone into the intervertebral implant with the greatest possible stability of the intervertebral implant overall.

It is favorable if the perforation defines a perforation longitudinal axis and if the perforation longitudinal axis runs transversely, in particular perpendicularly, to the first vertebral body abutment face and/or transversely, in particular perpendicularly, to the second vertebral body abutment face. In particular, the perforation longitudinal axis may run parallel to the support element longitudinal axes. Thus, in particular, a stability of the intervertebral implant can be further increased, independently of which cross sectional shape and size the perforation has.

In accordance with a further preferred embodiment of the present disclosure, provision may be made that the frame structure comprises a first self-enclosed inner frame part and a second self-enclosed inner frame part, and in that the at least two support elements connect the two inner frame parts to one another. Due to such a direct connection of the inner frame parts to the at least two support elements, a movement of the inner frame parts toward one another can be avoided. Overall, a stability of the intervertebral implant can thus be increased. In particular, more than two inner frame parts may be provided in order to further improve a torsional rigidity of the intervertebral implant.

The intervertebral implant can be made particularly compact if the two inner frame parts delimit the perforation at least in sections.

The intervertebral implant can be formed in a particularly simple manner if the first inner frame part is configured in the form of a ring and/or if the second inner frame part is configured in the form of a ring. The inner frame parts that are connected to the at least two support elements thus also define a position of the support elements on the intervertebral implant.

It is advantageous if the first inner frame part delimits the implant top side at least in sections and/or if the second inner frame part delimits the implant bottom side at least in sections. The inner frame parts may thus delimit an outer contour of the intervertebral implant at least in sections. Due to the connection of the at least two support elements to the inner frame parts, forces acting on the inner frame parts can thus be transmitted into the support elements, which helps to further improve a stability of the intervertebral implant.

It is favorable if the frame structure comprises a first self-enclosed outer frame part and a second self-enclosed outer frame part and if the two outer frame parts are connected, in particular in a torsionally resistant manner, to the two inner frame parts. Such a frame structure may define, in particular, an implant volume, which extends between the inner and the outer frame parts. This implant volume may be filled, e.g., by an open-pored lattice structure that enables the ingrowth of bone but does not have a stability, in particular compression stability, necessary for the function of the intervertebral implant. The frame structure serves in the intervertebral implant to ensure the stability of the intervertebral implant. The function of optimal ingrowth of bone tissue can thus, for example, be separated in a targeted, defined manner from a function of maximizing a stability of the intervertebral implant.

It is favorable if the first outer frame part delimits the implant top side at least in sections and/or if the second outer frame part delimits the implant bottom side at least in sections. The outer frame parts can thus dissipate forces acting on the intervertebral implant to the inner frame parts and thus indirectly to the support elements. In addition, the outer frame parts can delimit the intervertebral implant laterally as well. For example, three or more outer frame parts may also be provided, depending on the size of the intervertebral implant, which has a corresponding size, depending on the position of the intervertebral disc space into which it is to be inserted.

The intervertebral implant can be formed in a simple manner if the first outer frame part is configured in the form of a ring and/or if the second outer frame part is configured in the form of a ring. A ring does not necessarily have to have a circular shape. In particular, it may be of oval configuration or consist of a plurality of portions that have different curvatures, in particular it may also comprise rectilinear portions.

The intervertebral implant preferably comprises a frame base body, which connects the outer frame parts to the inner frame parts. The frame base body may be used, for example, for handling the intervertebral implant. In addition, it may contribute significantly to the stability of the intervertebral implant by being correspondingly designed.

In order to be able to achieve, in particular, a high stability of the intervertebral implant, it is advantageous if the frame base body is of solid configuration.

The intervertebral implant can be formed in a simple manner if the frame base body is of cuboidal or substantially cuboidal configuration.

For handling the intervertebral implant, it is favorable, in particular, if it comprises an instrument receptacle for being brought into force-locking and/or positive-locking engagement with an insertion instrument.

A handling of the intervertebral implant can be made simple and secure if the instrument receptacle is arranged or formed on the frame base body. In particular, the instrument receptacle may be accessible from a front side that extends between the implant top side and the implant bottom side transversely thereto.

It is advantageous if the instrument receptacle defines an instrument receptacle longitudinal axis and if the instrument receptacle longitudinal axis runs transversely, in particular perpendicularly, to the perforation longitudinal axis. This makes it possible, in particular, to bring the intervertebral implant into engagement with an insertion instrument and to insert it laterally into an intervertebral disc space. Both the implant bottom side and the implant top side can thereby remain completely free, so that the intervertebral implant can be inserted into the intervertebral disc space in an unhindered manner.

The intervertebral implant can be formed in a simple manner if the instrument receptacle is configured in the form of a bore or is formed by a sleeve.

A coupling of the intervertebral implant for the insertion thereof into an intervertebral disc space with an insertion instrument can be improved in a simple manner by the instrument receptacle being provided with an internal thread. The insertion instrument may then be provided with an external thread that corresponds to the internal thread of the instrument receptacle. It is thus possible to screw the insertion instrument to the intervertebral implant, thereby making it possible to temporarily produce a stable connection between the insertion instrument and the intervertebral implant.

In accordance with a further preferred embodiment of the present disclosure, provision may be made that a rear side of the intervertebral implant extends transversely, in particular perpendicularly, to the first vertebral body abutment face and transversely, in particular perpendicularly, to the second vertebral body abutment face. Thus, for example, overall a cuboidal or substantially cuboidal intervertebral implant can be formed.

The instrument receptacle preferably extends from the front side of the intervertebral implant to the perforation, in particular in parallel or substantially in parallel to the implant top side and/or to the implant bottom side. This enables, in particular, the formation or arrangement of the instrument receptacle on the intervertebral implant without sacrificing stability. The frame base body may, in particular, be of solid configuration except for the instrument receptacle in order to be able to ensure a greatest possible stability of the intervertebral implant.

The first vertebral body abutment face and/or the second vertebral body abutment face are preferably of planar or substantially planar configuration at least in sections, in particular completely. They can thus be optimally adapted to a side face of the vertebral body delimiting the intervertebral disc space in order to enable an optimal load capacity.

It is favorable if the first vertebral body abutment face defines a first abutment plane and if the second vertebral body abutment face defines a second abutment plane and if the first abutment plane and the second abutment plane extend in parallel to one another or are inclined relative to one another by an angle of inclination. This design makes it possible, in particular, to optimally adapt the intervertebral implant to the physiologically predetermined intervertebral disc space in order to keep the adjacent vertebral bodies at a desired distance and in a natural orientation relative to one another.

The angle of inclination preferably has a value in a range between 0° and about 20°. Such an angle of inclination makes it possible, in particular, to optimally adapt the intervertebral implant to the physiological conditions of the spine of the patient.

In accordance with a further preferred embodiment of the present disclosure, provision may be made that the first vertebral body abutment face and/or the second vertebral body abutment face are formed, at least in sections, in particular completely, convexly curved, in particular two- or three-dimensionally curved, facing away from the intervertebral implant. Forming the vertebral body abutment faces in the described manner enables, in particular, an optimal adaptation to natural conditions of an intervertebral disc of a patient in which the intervertebral implant is to be inserted into an intervertebral disc space that is cleared out.

To facilitate and improve the ingrowth of bone tissue into the intervertebral implant, it is favorable if an implant volume defined by the intervertebral implant is at least partially filled by an open-pored lattice structure. In particular, the implant volume may be completely filled by such an open-pored lattice structure. The lattice structure may be formed, in particular, by a wire-like fabric or a fabric structure, which has a multitude of cavities that are in fluidic connection with one another. Such a lattice structure can be formed in a simple manner, for example by a generative production method.

The lattice structure is favorably produced by a generative production method. This makes it possible, in particular, to form the intervertebral implant from one piece, i.e., in particular monolithically, namely both the supporting parts of the intervertebral implant, i.e., in particular the frame structure, and those parts that facilitate the ingrowth of bone tissue into the intervertebral implant like, in particular, an open-pored lattice structure. In the present application, the term "generative" is used synonymously with the term "additive".

The production of the intervertebral implant can be improved overall if the intervertebral implant as a whole and/or the frame structure are formed by a generative production method. In particular, an open-pored lattice structure of the intervertebral implant, if such a structure is provided, can be formed by the generative production method.

The frame structure and/or the lattice structure and/or the intervertebral implant as a whole are favorably formed by selective laser sintering. The intervertebral implant can thus, for example, be built in layers. In particular, any structures can be formed.

In accordance with a further preferred embodiment of the present disclosure, provision may be made that the frame structure and/or the intervertebral implant as a whole are made of a metallic material and/or a plastic material. In particular, the lattice structure, which may be of open-pored configuration, may be made of a metallic material and/or a plastic material.

Further, the present disclosure relates to an intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body, wherein the intervertebral implant comprises a frame structure with at least two support elements, wherein the at least two support elements extend from the implant top side to the implant bottom side, wherein the at least two support elements define support element longitudinal axes, which run transversely, in particular perpendicularly, to at least one of the first vertebral body abutment face and the second vertebral body abutment face, wherein the frame structure comprises a first self-enclosed inner frame part and a second self-enclosed inner frame part, and wherein the at least two support elements connect the two inner frame parts to one another by a direct connection of the inner frame parts to the at least two support elements.

Moreover, the present disclosure relates to an intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body, wherein the intervertebral implant comprises a frame structure with at least two support elements, wherein the at least two support elements extend from the implant top side to the implant bottom side, wherein the at least two support elements define support element longitudinal axes, which run transversely, in particular perpendicularly, to at least one of the first vertebral body abutment face and the second vertebral body abutment face, wherein the frame structure comprises a first self-enclosed inner frame part and a second self-enclosed inner frame part, wherein the at least two support elements connect the two inner frame parts to one another, and wherein the at least two support elements define a cross sectional area that is constant or substantially constant along its extent.

Depicted in FIG. 1 is a schematic perspective total view of a first embodiment of an intervertebral implant that is denoted as a whole with the reference numeral 10.

The intervertebral implant 10 is configured for insertion into an intervertebral disc space 12 between two adjacent vertebral bodies 14 and 16 of a human or animal spine 18.

The intervertebral implant 10 has an implant top side 20 and an implant bottom side 22.

The implant top side 20 defines a first vertebral body abutment face 24 for abutting against the vertebral body 14. The implant bottom side 22 defines a second vertebral body abutment face 26 for abutting against the vertebral body 16.

The intervertebral implant 10 further comprises a frame structure 28 with at least two support elements 30. In the embodiment of the intervertebral implant 10 depicted in FIGS. 1 to 4, a total of four support elements 30 are provided.

The support elements 30 extend from the implant top side 20 to the implant bottom side 22.

The support elements 30 define support element longitudinal axes 32, which run transversely to the vertebral body abutment faces 24 and 26. In the embodiment depicted in FIGS. 1 to 4, the support element longitudinal axes 32 extend perpendicularly to the second vertebral body abutment face 26. Furthermore, the support element longitudinal axes 32 run perpendicularly to a tangential plane 34, which abuts against the first vertebral body abutment face 24 that is convexly curved facing away from the intervertebral implant 10.

The frame structure 28 comprises a first self-enclosed inner frame part 36 and a second self-enclosed inner frame part 38. The support elements 30 connect the two frame parts 36 and 38 to one another. The frame parts 36 and 38 are each configured in the form of a respective ring 40 and 42.

The first inner frame part 36 forms part of the implant top side 20 or delimits said side in sections, namely in the form of the ring 40. In an analogous manner, the second inner frame part 38 delimits the implant bottom side 22 in sections or forms part of the implant bottom side 22.

The intervertebral implant 10 has a central perforation 44, which extends from the implant top side 20 to the implant bottom side 22 through the intervertebral implant 10. The perforation 44 is of hollow-cylindrical or substantially hollow-cylindrical configuration.

In other embodiments, the perforation 44 has an oval or rectangular, in particular square, cross section.

The perforation 44 defines a perforation longitudinal axis 46, which runs transversely to the first vertebral body abutment face 24 and transversely to the second vertebral body abutment face 26. In the embodiment of the intervertebral implant 10 depicted in FIGS. 1 to 4, the perforation longitudinal axis 46 runs perpendicularly to the second vertebral body abutment face 26 and perpendicularly to the tangential plane 34 against the first vertebral body abutment face 24 that is convexly curved facing away from the intervertebral implant 10.

The two inner frame parts 36 and 38 delimit the perforation 44 in sections.

The support elements 30 keep the frame parts 36 and 38 at a defined distance 48 from one another.

The intervertebral implant 10 overall is of mirror-symmetrical configuration in relation to a mirror plane 50, which extends perpendicularly to the first vertebral body abutment face 24.

The frame structure 28 further comprises a self-enclosed first outer frame part 52 and a second self-enclosed outer frame part 54. The outer frame parts 52 and 54 are connected to the inner frame parts 36 and 38. The frame structure 28 overall is of torsionally resistant configuration.

The first outer frame part 52 delimits the implant top side 20 in sections or forms part of the implant top side 20. In an analogous manner, the second outer frame part 54 delimits the implant bottom side 22 in sections or forms part thereof.

The frame parts 52 and 54 are each configured in the form of a respective ring 56 and 58. The rings 56 and 58 are namely of self-enclosed, but not circular configuration. They are composed of a plurality of portions with different radii of curvature, wherein portions of the rings 56 and 58 adjoining a rear side 60 of the intervertebral implant 10 run rectilinearly, wherein these portions with longitudinal axes defined thereby run perpendicularly to the support element longitudinal axes 32 and in parallel to the second vertebral body abutment face 26.

The frame structure 28 further comprises a frame base body 62, which is of solid configuration and connects the outer frame parts 52 and 54 to the inner frame parts 36, 38.

The frame base body 62 is of substantially cuboidal configuration and extends from a plate-shaped front side 64 to the perforation 44, namely from the implant top side 20 to the implant bottom side 22.

The intervertebral implant 10 further comprises an instrument receptacle 66 for being brought into force-locking and/or positive-locking engagement with an insertion instrument that is not depicted in the Figures.

The instrument receptacle 66 is arranged or formed on the frame base body 62 and defines an instrument receptacle longitudinal axis 68, which runs transversely, namely perpendicularly in the embodiment of the intervertebral implant 10 depicted in FIGS. 1 to 4, to the perforation longitudinal axis 46.

The instrument receptacle 66 is configured in the form of a bore 70. In a further embodiment, the instrument receptacle is formed by a sleeve. Furthermore, the instrument receptacle 66 is provided with an internal thread 72.

The front side 64 of the intervertebral implant 10 extends transversely to the first vertebral body abutment face 24, in particular perpendicularly to the tangential plane 34, and transversely, namely perpendicularly, to the second vertebral body abutment face 26.

The instrument receptacle 66 extends from the front side 64 to the perforation 44, namely in parallel to the implant bottom side 22.

The first vertebral body abutment face 24 is of planar configuration in sections. The second vertebral body abutment face 26 is completely of planar configuration.

The first vertebral body abutment face 24 defines a first abutment plane 74, which extends commencing from the rear side 60 on a short portion of the implant top side 20 in the direction toward the front side 64.

The second vertebral body abutment face 26 defines a second abutment plane 76. In the depicted embodiment of the intervertebral implant 10, the abutment planes 74 and 76 are inclined relative to one another by an angle of inclination 78. The angle of inclination 78 has a value in a range between 0° and about 20°.

The first vertebral body abutment face 24 is convexly curved in sections, namely two-dimensionally or three-dimensionally curved, facing away from the intervertebral implant 10.

The support elements 30 have end faces 80 and 82 that face away from the intervertebral implant 10. The end faces 80 and 82 form part of the first vertebral body abutment face 24 and the second vertebral body abutment face 26, respectively.

A respective anchoring projection 84 and 86 is arranged on the end faces 80 and 82. The anchoring projections 84 and 86 are of pointed configuration and each define a respective tip 88 and 90. Overall, the anchoring projections 84 and 86 are of conical or substantially conical configuration.

The anchoring projections 84 and 86 define projection longitudinal axes 92, which run in parallel to the support element longitudinal axes 32 of the associated support elements 30.

A cross section of the support elements 30 in relation to the respective support element longitudinal axis 32 is formed by a combination of a rectangle and a semicircle. The semicircle is directed pointing away from the perforation 44 in the direction toward the outer frame parts 52 and 54. The anchoring projections 84 and 86 are arranged or oriented with their base face in relation to the end faces 80 and 82 such that the semicircle covers half of the respective base face.

The support elements 30 overall are each of solid configuration. They have no cavities.

The intervertebral implant 10 and the frame structure 28 are formed by an additive production method. If the intervertebral implant 10 is made of a metallic material, it is formed additively, for example by selective laser sintering or electron beam melting. An intervertebral implant 10 made of a plastic material is formed, for example, by 3D printing.

Schematically depicted in FIGS. 5 to 8 is a further embodiment of an intervertebral implant that is also denoted with the reference numeral 10. It corresponds in its structure basically with the intervertebral implant depicted in FIGS. 1 to 4, such that to denote individual elements the same reference numerals were used as in the embodiment depicted in FIGS. 1 to 4.

The embodiment depicted in FIGS. 5 to 8 differs only in its dimensions from the embodiment depicted in FIGS. 1 to 4. This is made clear, in particular, by the different height 94 that defines a distance between the first vertebral body abutment face 24 and the second vertebral body abutment face 26 in the region of the front side 64.

The size difference of the two embodiments of the intervertebral implants 10 depicted in FIGS. 1 to 8 becomes particularly clear when one considers that the instrument receptacle 66 is identically dimensioned in both embodiments. It thus follows, in particular, directly that the height 94 in the embodiment of FIGS. 5 to 8 is only about just 40% of the height 94 in the embodiment of FIGS. 1 to 4.

A further embodiment of an intervertebral implant, denoted as a whole with the reference numeral 10, is depicted in FIGS. 9 to 15. It corresponds in its structure completely with the embodiment of FIGS. 5 to 8. In addition, the implant volume defined by the intervertebral implant 10, except for the perforation 44 and the instrument receptacle 66, is filled with an open-pored lattice structure 96.

The lattice structure 96 has a multitude of cavities in fluidic connection with one another, into which bone tissue of the implanted intervertebral implant can grow.

Figure 9:
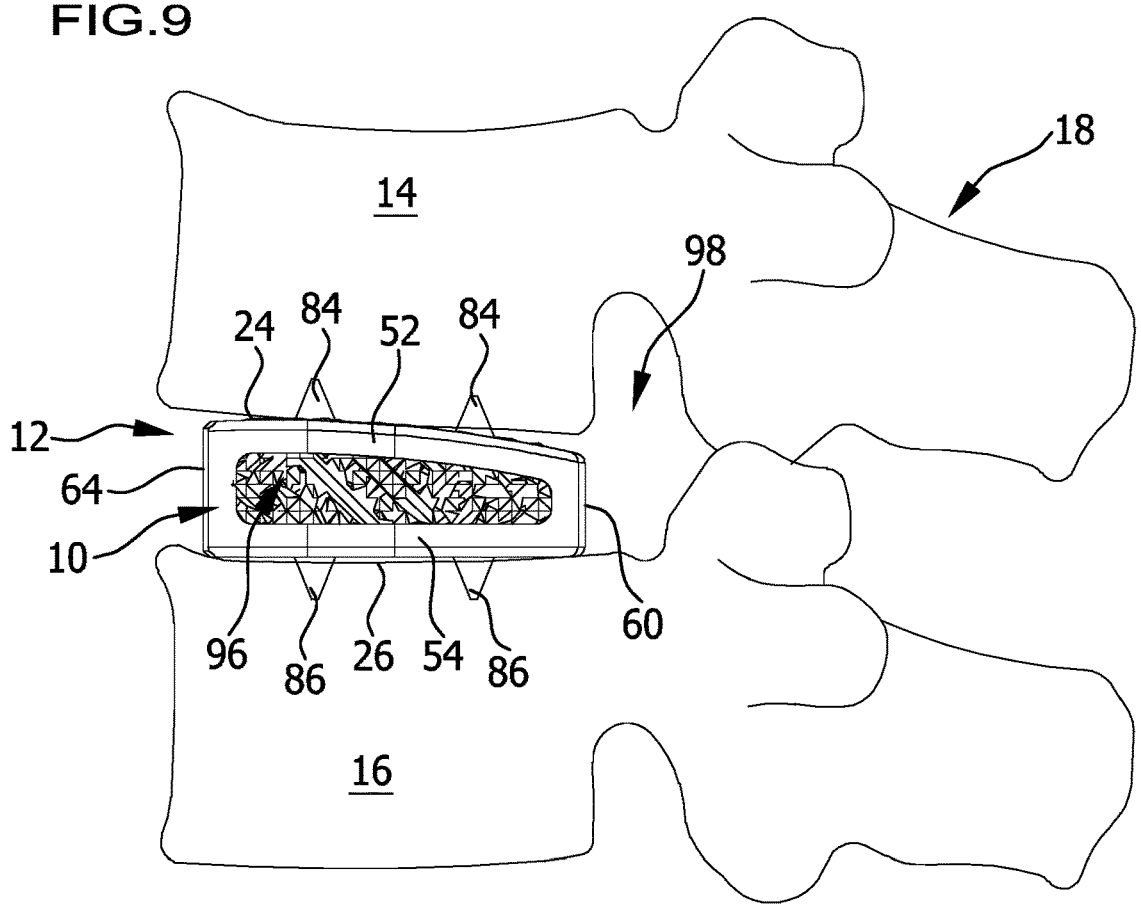
FIG. 9 is a schematic side view of two adjacent vertebrae of a human spine with an intervertebral implant inserted into an intervertebral disc space between the vertebrae.
Figure 10:
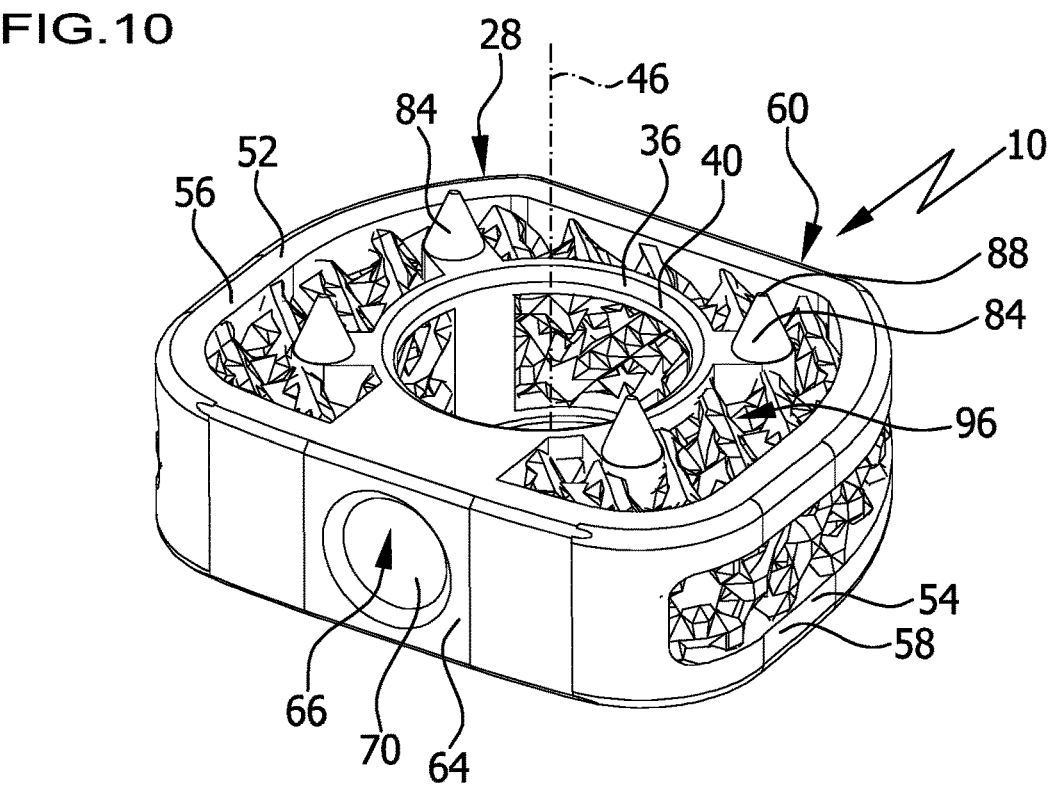
FIG. 10 is a schematic perspective total view of the intervertebral implant from FIG. 9.
Figure 11:
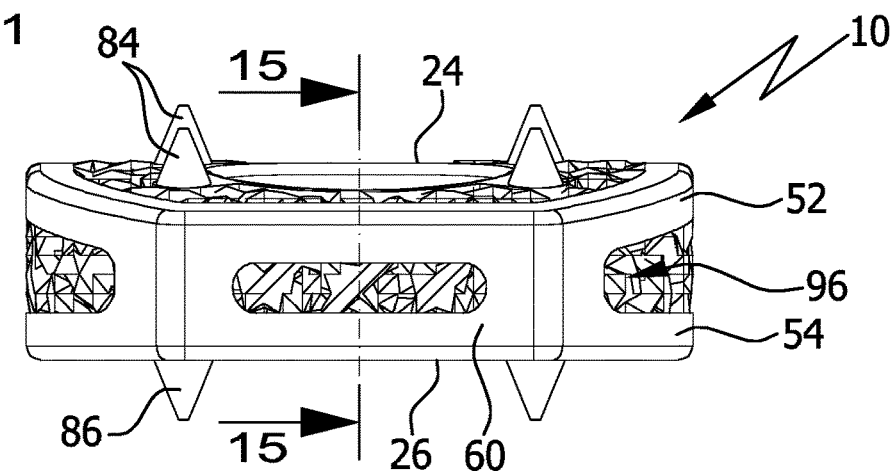
FIG. 11 is a view of the intervertebral implant from FIG. 10 from behind in the direction of the arrow A from FIG. 12.
Figure 12:
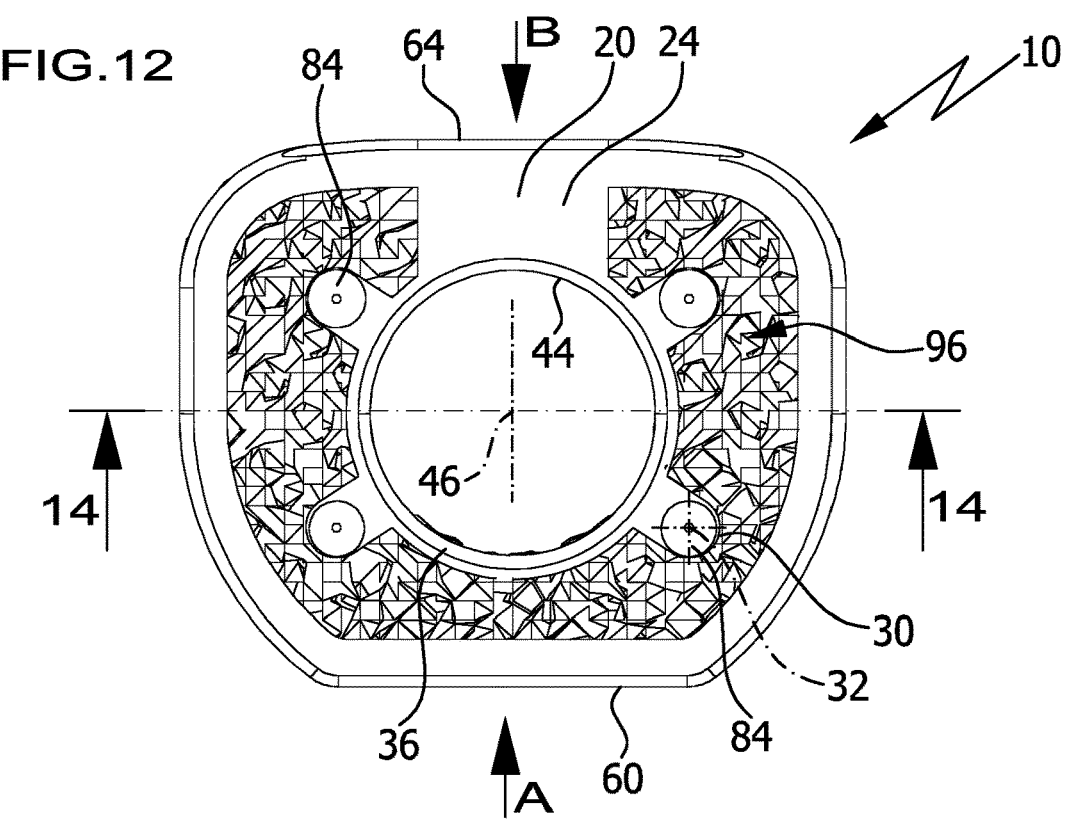
FIG. 12 is a plan view of the intervertebral implant from FIG. 10 from above.
Figure 13:
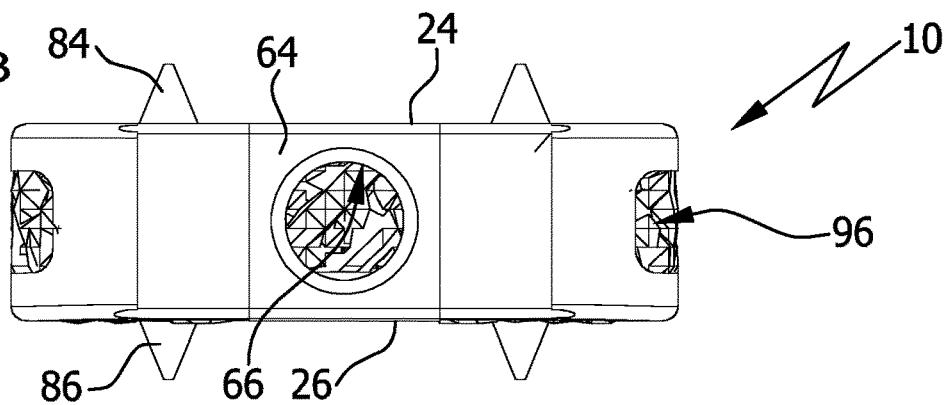
FIG. 13 is a view of the intervertebral implant from FIG. 10 from the front in the direction of the arrow B from FIG. 12.
Figure 14:
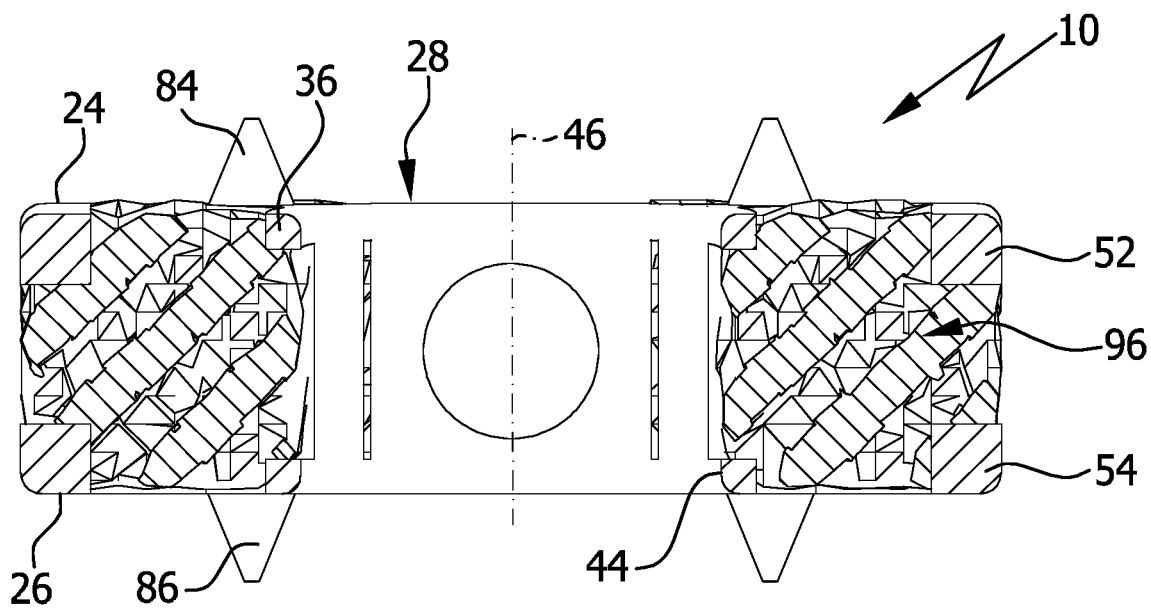
FIG. 14 is a cut view of the intervertebral implant from FIG. 12 along line 14-14.
Figure 15:
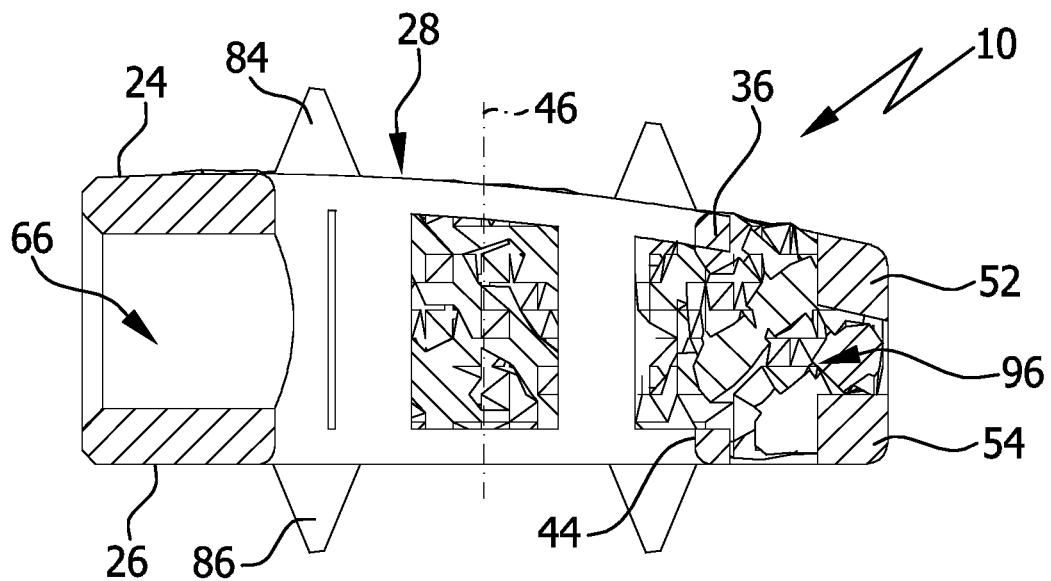
FIG. 15 is a cut view of the intervertebral implant from FIG. 11 along line 15-15.

FIG. 9 shows schematically the intervertebral implant 10 that is inserted into the intervertebral disc space 12 between the vertebral bodies 14 and 16. The anchoring projections 84 and 86 penetrate into the vertebral bodies 14 and 16 and prevent a movement of the intervertebral implant 10, in particular, in a direction parallel to the respective vertebral body abutment faces 24 and 26 and thus, in particular, also in the direction toward a spinal canal 98 of the spine 18.

The intervertebral implant 10 is inserted into the intervertebral disc space 12, i.e., the intervertebral space between the vertebral bodies 14 and 16, in such a way that the front side 64 faces in the distal or anterior direction, i.e., in the direction toward, e.g., an abdomen of a patient, and the rear side 60 faces in the dorsal direction, i.e., in the direction toward the spinal canal 98, if the vertebral bodies 14 and 16 are vertebral bodies of lumbar vertebrae.

The intervertebral implant 10 in accordance with the embodiment depicted in FIGS. 1 to 4 can also be filled with a lattice structure 96 that is described in connection with the embodiment of FIGS. 9 to 15, namely in particular completely or only in the region of the implant volume defined by the intervertebral implant 10 with the exception of the perforation 44 and the instrument receptacle 66.

All described embodiments of intervertebral implants 10 have in common, in particular, that the anchoring projections 84 and 86 are solidly connected to the frame structure 28. Thus, they cannot be pressed into the volume defined by the respective intervertebral implant 10, as would be the case if the anchoring projections were to be arranged in the region, i.e., directly on the lattice structure 96. Shearing off or so-called sinking of the anchoring projections in the implant volume can thus be prevented. Overall, a significantly improved stability of the intervertebral implant with outstanding properties for the ingrowth of bone tissue into the intervertebral implant can be achieved.

The solid configuration of the support elements, which form bases for the anchoring projections 84 and 86, facilitates the cleaning of the lattice structure 96. In particular, the washing out of the intervertebral implants 10 after production, in particular for removing auxiliary agent residues, is improved because unwashable areas due to the anchoring projections 84 and 86 have been reduced to a minimal level. Unwashable areas can arise, in particular, if the anchoring projections were to be placed directly on the lattice structure 96, such that cavities that are difficult to clean would remain behind the anchoring projections 84 and 86.

REFERENCE NUMERAL LIST 10 intervertebral implant
12 intervertebral disc space 14 vertebral body
16 vertebral body
18 spine
20 implant top side
22 implant bottom side
24 first vertebral body abutment face
26 second vertebral body abutment face
28 frame structure
30 support element
32 support element longitudinal axis
34 tangential plane
36 first inner frame part
38 second inner frame part
40 ring
42 ring
44 perforation
46 perforation longitudinal axis
48 distance
50 mirror plane
52 first outer frame part
54 second outer frame part
56 ring
58 ring
60 rear side
62 frame base body
64 front side
66 instrument receptacle
68 instrument receptacle longitudinal axis
70 bore
72 internal thread
74 abutment plane
76 abutment plane
78 angle of inclination
80 end face
82 end face
84 anchoring projection
86 anchoring projection
88 tip
90 tip
92 projection longitudinal axis
94 height
96 lattice structure
98 spinal canal

The invention claimed is:

1. An intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body, wherein the intervertebral implant comprises a frame structure with at least two support elements, wherein the at least two support elements extend from the implant top side to the implant bottom side, wherein each of the at least two support elements extends rectilinearly along a respective support element longitudinal axis that extends transversely to at least one of the first vertebral body abutment face and the second vertebral body abutment face, wherein each of the at least two support elements has a respective first end face that faces away from the intervertebral implant and forms part of the first vertebral body abutment face and a respective second end face that faces away from the intervertebral implant and forms part of the second vertebral body abutment face, and each of the at least two support elements extends rectilinearly an entire distance from the respective first end face to the respective second end face, wherein the frame structure comprises a first self-enclosed inner frame part and a second self-enclosed inner frame part, and wherein the at least two support elements connect the first inner frame part and the second inner frame part to one another by a direct rectilinear connection of the first inner frame part and the second inner frame part to the at least two support elements.

2. The intervertebral implant according to claim 1, wherein the at least two support elements have end faces that face away from the intervertebral implant and wherein at least one of these end faces bears at least one anchoring projection pointing away from the intervertebral implant.

3. The intervertebral implant according to claim 2, wherein the at least one anchoring projection defines a projection longitudinal axis and wherein the projection longitudinal axis runs in parallel or substantially in parallel to the support element longitudinal axis of the respective support element.

4. The intervertebral implant according to claim 1, wherein the at least two support elements define a cross section in relation to the respective support element longitudinal axis, which is rectangular, triangular, or circular, or is formed by a combination of a rectangle and a semicircle.

5. The intervertebral implant according to claim 1, wherein at least one of:
a) the at least two support elements are of solid configuration; and
b) the intervertebral implant has a central perforation that extends from the implant top side to the implant bottom side through the intervertebral implant.

6. The intervertebral implant according to claim 1, wherein the intervertebral implant has a central perforation that extends from the implant top side to the implant bottom side through the intervertebral implant, and the first inner frame part and the second inner frame part at least partly delimit the perforation.

7. The intervertebral implant according to claim 6, wherein at least one of:
a) the first inner frame part is configured in the form of a ring; and
b) the second inner frame part is configured in the form of a ring.

8. The intervertebral implant according to claim 6, wherein at least one of:
a) the first inner frame part at least partly delimits the implant top side; and
b) the second inner frame part at least partly delimits the implant bottom side.

9. The intervertebral implant according to claim 6, wherein the frame structure comprises a first self-enclosed outer frame part and a second self-enclosed outer frame part, and wherein the first outer frame part and the second outer frame part are connected to the first inner frame part and the second inner frame part.

10. The intervertebral implant according to claim 9, wherein at least one of:
a) the first outer frame part at least partly delimits the implant top side; and
b) the second outer frame part at least partly delimits the implant bottom side.

11. The intervertebral implant according to claim 9, wherein at least one of:
a) the first outer frame part is configured in the form of a ring; and
b) the second outer frame part is configured in the form of a ring.

12. The intervertebral implant according to claim 9, wherein the intervertebral implant comprises a frame base body and wherein the frame base body connects the first outer frame part and the second outer frame part to the first inner frame part and the second inner frame part,
wherein the frame base body comprises at least one of:
a) a solid configuration; and
b) a cuboidal configuration.

13. The intervertebral implant according to claim 1, wherein:
the intervertebral implant comprises an instrument receptacle for being brought into at least one of force-locking and positive-locking engagement with an insertion instrument,
the intervertebral implant comprises a frame base body that connects the first inner frame part and the second inner frame part to a first outer frame part and a second outer frame part, and
wherein the instrument receptacle is arranged or formed on the frame base body.

14. The intervertebral implant according to claim 1, wherein an implant volume defined by the intervertebral implant is at least partially filled by an open-pored lattice structure.

15. The intervertebral implant according to claim 1, wherein the at least two support elements define a cross sectional area that is constant or substantially constant along its extent.

16. An intervertebral implant for insertion into an intervertebral disc space between two adjacent vertebral bodies of a human or animal spine, wherein the intervertebral implant has an implant top side, which defines a first vertebral body abutment face for abutting against a first vertebral body, and an implant bottom side, which defines a second vertebral body abutment face for abutting against a second vertebral body, wherein the intervertebral implant comprises a frame structure with at least two support elements, wherein the at least two support elements extend from the implant top side to the implant bottom side, wherein the at least two support elements define support element longitudinal axes, which run transversely to at least one of the first vertebral body abutment face and the second vertebral body abutment face, wherein the frame structure comprises a first self-enclosed inner frame part and a second self-enclosed inner frame part, wherein the at least two support elements connect the first inner frame part and the second inner frame part to one another, wherein each of the at least two support elements has a respective first end face that faces away from the intervertebral implant and forms part of the first vertebral body abutment face and a respective second end face that faces away from the intervertebral implant and forms part of the second vertebral body abutment face, and wherein the at least two support elements define a cross sectional area that is constant or substantially constant along its extent.

17. The intervertebral implant according to claim 16, wherein the frame structure comprises a first self-enclosed outer frame part and a second self-enclosed outer frame part, and wherein the first outer frame part and the second outer frame part are connected to the first inner frame part and the second inner frame part.

18. The intervertebral implant according to claim 17, wherein the intervertebral implant comprises a frame base body and wherein the frame base body connects the first outer frame part and the second outer frame part to the first inner frame part and the second inner frame part.

19. The intervertebral implant according to claim 16, wherein the at least two support elements have end faces that face away from the intervertebral implant and wherein at least one of the end faces bears at least one anchoring projection pointing away from the intervertebral implant.

20. The intervertebral implant according to claim 19, wherein the at least one anchoring projection defines a projection longitudinal axis and wherein the projection longitudinal axis runs in parallel or substantially in parallel to a support element longitudinal axis of the respective support element.

* * * * *